(12) United States Patent
Harada (10) Patent No.: US 7,071,626 B2
(45) Date of Patent: Jul. 4, 2006

(54) PLASMA GENERATOR

(75) Inventor: Manabu Harada, Tokyo (JP)

(73) Assignee: Kabushiki Kaisha Marukomu, Tokyo (JP)

( * ) Notice: Subject to any disclaimer, the term of this patent is extended or adjusted under 35 U.S.C. 154(b) by 217 days.

(21) Appl. No.: 10/759,955

(22) Filed: Jan. 16, 2004

(65) Prior Publication Data

US 2005/0099134 A1    May 12, 2005

(30) Foreign Application Priority Data

Nov. 10, 2003    (JP)    .............................. 2003-380100

(51) Int. Cl.
*H01J 7/24*    (2006.01)

(52) U.S. Cl. ............................ 315/111.21; 315/111.31; 315/111.91; 422/186.03; 422/186.07; 422/186.21

(58) Field of Classification Search ........... 315/111.21, 315/111.81, 111.91, 169.1, 177; 422/186.03, 422/186.04, 186.07, 186.16, 186.21; 118/723 E; 156/345.43, 345.44, 345.47

See application file for complete search history.

(56) References Cited

U.S. PATENT DOCUMENTS 4,626,876 A * 12/1986 Miyagawa et al. ......... 347/140
5,004,587 A * 4/1991 Tacchi .................... 422/186.19
5,637,180 A * 6/1997 Gosain et al. .......... 156/345.47
5,759,497 A * 6/1998 Kuzumoto et al. ..... 422/186.07
6,199,505 B1 * 3/2001 Sato et al. ............... 118/723 E
6,764,658 B1 * 7/2004 Denes et al. ........... 422/186.04

FOREIGN PATENT DOCUMENTS

| JP | 2002-001055 A | 1/2002 |
| JP | 2002-078788 A | 3/2002 |
| JP | 2003-135571 A | 5/2003 |

OTHER PUBLICATIONS

J. W. Keto: Electron Beam Excited Mixtures of $O_2$ in Argon. II. Electron Distributions and Excitation Rates, J. Chem. Phys. 74(8), Apr. 15, 1981, American Institute of Physics, pp. 4445-4449.

* cited by examiner

*Primary Examiner*—Haissa Philogene
(74) *Attorney, Agent, or Firm*—Frishauf, Holtz, Goodman & Chick, P.C.

(57)    ABSTRACT

Disclosed herein is a plasma generator, in which a plasma forming space, into which the air is introduced, is provided, band plate-like first and second electrodes are arranged in opposed relation to each other through a dielectric in the plasma forming space, and plasma is generated by discharge caused by applying voltage between the first and second electrodes, wherein the first and second electrodes are arranged in a state relatively displaced in a surface direction of the dielectric so as to satisfy the specific relationship.

16 Claims, 3 Drawing Sheets

PRIOR ART

PLASMA GENERATOR

BACKGROUND OF THE INVENTION

1. Field of the Invention

The present invention relates to a plasma generator, and particularly to a plasma generator suitable for use, for example, in decomposing or removing substances harmful to the human body, which are contained in the air, by generating plasma by discharge between a pair of electrodes to form activated species.

2. Description of the Background Art

At present, plasma is considered to be useful as a medium capable of effectively removing or decomposing harmful substances contained in the air, for example, bacteria, viruses, pollen and/or the like, to make them harmless, since ions or activated species such as radicals formed by an electronic collision in the plasma facilitate chemical reactions with other atoms or molecules, and is thus used in, for example, deodorizing apparatus, bactericidal apparatus, air cleaning apparatus and the like (see, for example, Japanese Patent Application Laid-Open Nos. 2002-1055, 2003-135571 and 2002-78788).

Figure 6:
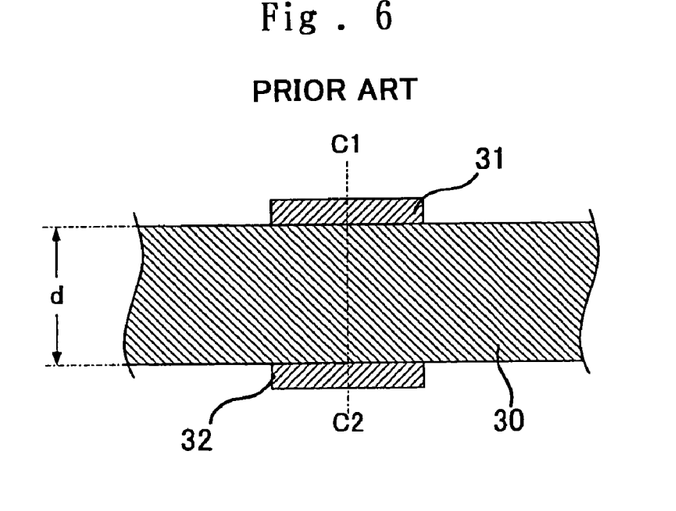
FIG. 6 is a sectional view schematically illustrating the construction of a conventional exemplary electrode structure.

Some plasma generators making up such deodorizing apparatus and air cleaning apparatus are constructed by providing an electrode structure that a pair of electrodes 31 and 32 are arranged in opposed relation to each other in a state that central positions C1 and C2 in arrangement of these electrodes are aligned with each other through a dielectric 30 composed of, for example, ceramic or quartz glass as illustrated in FIG. 6, and plasma is generated along the surface(s) of the dielectric 30 by discharge caused by applying voltage between the electrodes 31 and 32.

In the plasma generator utilizing the discharge (gaseous discharge) making use of the dielectric, however, ozone is unavoidably generated with the discharge between the electrodes. Since ozone is harmful to the human body, it is necessary to prevent or control the generation of ozone in the case where such a plasma generator is applied to, for example, a deodorizing apparatus, bactericidal apparatus or air cleaning apparatus. The environmental criteria as to ozone prescribed by, for example, Japan Air Cleaning Association is at most 0.05 ppm.

SUMMARY OF THE INVENTION

The present invention has been made on the basis of the foregoing circumstances and has as its object the provision of a plasma generator having a novel structure that plasma is generated by discharge between a pair of electrodes arranged through a dielectric, and an effect for decomposing or removing harmful substances contained in the air can be surely developed while surely preventing or controlling generation of ozone with the discharge.

According to the present invention, there is provided a plasma generator, in which a plasma forming space, into which the air is introduced, is provided, band plate-like first and second electrodes are arranged in opposed relation to each other through a dielectric in the plasma forming space, and plasma is generated by discharge caused by applying voltage between the first and second electrodes, wherein the first and second electrodes are provided on one surface and another surface of the dielectric, respectively, and arranged in a state relatively displaced in a surface direction of the dielectric so as to satisfy the following Equation 1 to Equation 3:

$$\tan\theta_2 = \frac{L1}{d} \quad \text{(Equation 1)}$$

$$\tan\theta_1 = \frac{1}{\varepsilon_2}\tan\theta_2 \quad \text{(Equation 2)}$$

$$26 \times 10^6 [\text{V/m}] \geq \frac{\cos\theta_1 \cdot \sin 2\theta_2}{d \sin 2\theta_1} V = E_1(\max) \quad \text{(Equation 3)}$$

wherein L1 is a separate distance between a front end edge position of the first electrode and a corresponding end edge position of the second electrode, which is located on an outside in a displacement direction of the electrodes from the front end edge position of the first electrode and closest to the front end edge position of the first electrode, in the surface direction of the dielectric, $\theta_2$ is an angle formed by an imaginary plane including the front end edge of the first electrode and the end edge of the second electrode with a thickness-wise direction of the dielectric, d is a thickness [m] of the dielectric, V is the intensity [V] of voltage applied between the first and second electrodes, $\theta_1$ is an outgoing angle of an electric field in the plasma forming space at a boundary surface of the dielectric, $\varepsilon_2$ is a dielectric constant of the dielectric, and $E_1(\max)$ is a maximum value [V/m] of the electric field at the end surface of the electrode.

In the plasma generator according to the present invention, the corresponding end edge of the second electrode may be formed by a rear edge or front edge of the second electrode.

In the plasma generator according to the present invention, the angle $\theta_2$ formed by the imaginary plane with the thickness-wise direction of the dielectric may preferably be at least 45°.

In the plasma generator according to the present invention, a ratio (L1/d) of the separate distance L1 to the thickness d of the dielectric may preferably be 1 to 3.

In the plasma generator according to the present invention, the voltage applied between the first and second electrodes may preferably be 2.5 to 3.5 kV.

According to the present invention, there is also provided a plasma generator which is provided with a plasma forming space, into which the air is introduced, and has, in the plasma forming space, an electrode arrangement structure that band plate-like first and second electrodes are arranged in spaced relation from each other in the same plane in the sectional thickness of the dielectric, and the following Equation 4 is satisfied:

$$26 \times 10^6 [\text{V/m}] \geq \frac{V}{L2} \quad \text{(Equation 4)}$$

wherein L2 is a separate distance [m] between the first electrode and the second electrode, and V is voltage [V] applied between the first and second electrodes.

According to the present invention, there is also provided a plasma generator which is provided with a plasma forming space, into which the air is introduced, and has, in the plasma forming space, an electrode arrangement structure that band plate-like first and second electrodes are arranged in spaced relation from each other are formed on a surface of the dielectric, a surface of at least either one of the first and second electrodes, being coated with a dielectric film, and the following Equation 4 is satisfied:

$$26 \times 10^6 [V/m] \geq \frac{V}{L2} \tag{Equation 4}$$

wherein L2 is a separate distance [m] between the first electrode and the second electrode, and V is voltage [V] applied between the first and second electrodes.

According to the plasma generators of the present invention, since an average value of electronic energy in a discharge field (electric field in the air) is controlled to a prescribed value or smaller by having the electrode arrangement structure satisfying the specific conditions, a collision cross section of ozone molecule becomes great to the electron in the discharge field, so that a collision with the ozone is easy to be caused, with a result that decomposition of ozone is facilitated by the collision of the low-energy electron. Generation of ozone with discharge is thus surely prevented or controlled, while the energy of the low-energy electron is increased by increasing the number of times of elastic collisions with gaseous molecules, with a result that such an electron contributes to decomposition of oxygen to surely form activated oxygen species, so that a required essential effect for decomposing or removing harmful substances contained in the air is surely developed.

In addition, the intensity of electronic energy in the discharge field can be controlled low without greatly lowering an electrostatic capacity by arranging the first and second electrodes in a state displaced from each other, so that an efficiency for forming activated species by function of plasma may not be lowered. Accordingly, a desired decomposing effect on harmful substances contained in the air is achieved, and moreover a decomposing effect on ozone is surely developed.

BRIEF DESCRIPTION OF THE DRAWING

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described in details with reference to the accompanying drawings.

Figure 1:
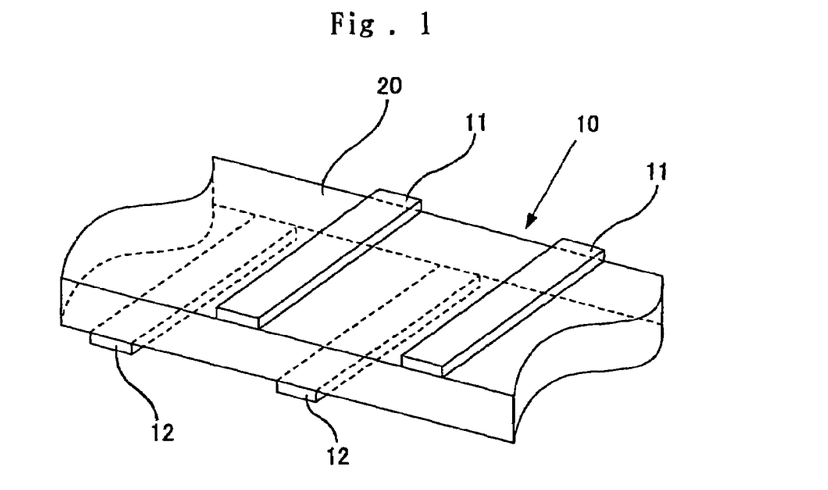
FIG. 1 is a perspective view schematically illustrating the construction of an exemplary electrode structure in a plasma generator according to the present invention.
Figure 2:
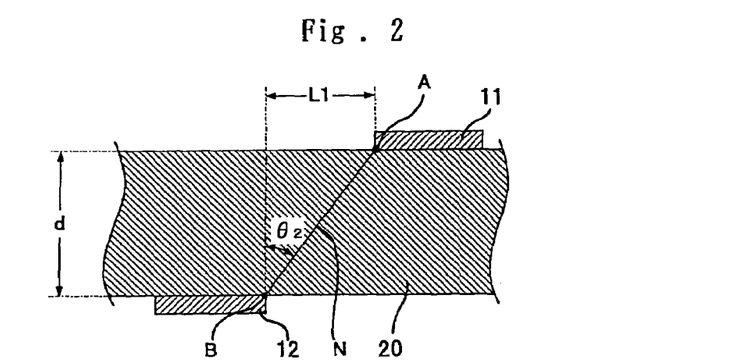
FIG. 2 is a sectional view illustrating a central section along width-wise direction of the electrode in the electrode structure shown in FIG. 1.

FIG. 1 is a perspective view schematically illustrating the construction of an exemplary electrode structure in a plasma generator according to the present invention, and FIG. 2 is a sectional view illustrating a central section along width-wise direction of the electrode in the electrode structure shown in FIG. 1.

This plasma generator is equipped with a plasma forming space into which the air containing harmful substances is introduced. The plasma forming space is formed by, for example, a glass vessel or the like. In the plasma forming space, an electrode structure 10 is provided that is constructed by a dielectric 20 in the form of, for example, a flat plate, a plurality of band plate-like first electrodes 11 arranged in spaced relation in a surface direction (longitudinal direction in FIG. 2) of the dielectric 20 on one surface of the dielectric 20 so as to be parallel to each other and a plurality of band plate-like second electrodes 12 arranged on another surface of the dielectric 20, each of which constitutes an electrode pair with a corresponding one of the first electrodes 11 through the dielectric 20. A voltage applying means (not illustrated) is connected between the first electrodes 11 and second electrodes 12. Each of the second electrodes 12 is arranged in a state that a position of the corresponding end edge B, which is positioned at a right end of the electrode 12 in FIG. 2, is located on an outside in a displacement direction of the electrodes from the position of the front end edge (left end edge in FIG. 2) A of the first electrode 11. In the present invention, the first electrodes 11 and the second electrodes 12 are preferably arranged at regular intervals so that plasma can be substantially uniformly generated.

As a material forming the dielectric 20, may be used a conventionally used material. As examples thereof, may be mentioned insulating materials such as ceramics and glass.

As a material forming the first electrodes 11 and second electrodes 12, is used a conductor, for example, a metal such as a stainless steel.

As the voltage applying means, is used, for example, a transformer operated by a commercial power source of 100 V or the like. The voltage applying means is so constructed voltage raised to, for example, 2.5 to 3.5 kV is applied between the first and second electrodes.

In each pair of electrodes in this electrode structure 10, the first electrode 11 and the second electrodes 12 are arranged relatively displaced to each other in an arranging direction of the electrodes so as to satisfy the following Equation 1 to Equation 3:

$$\tan\theta_2 = \frac{L1}{d} \tag{Equation 1}$$

$$\tan\theta_1 = \frac{1}{\varepsilon_2}\tan\theta_2 \quad \text{(Equation 2)}$$

$$26\times10^6[\text{V/m}] \geqq \frac{\cos\theta_1 \cdot \sin2\theta_2}{d\sin2\theta_1} V = E_1(\text{max}) \quad \text{(Equation 3)}$$

In Equation 1 to Equation 3, L1 is a separate distance (hereinafter referred to as "displacement quantity") between a position (position of a left end edge of the first electrode 11 in this embodiment) of the front end edge A of the first electrode 11 on one surface (the upper surface) of the dielectric 20 and a position (position of a right end edge of the second electrode 12 in this embodiment) of corresponding end edge B of the second electrode 12 on the another surface (the lower surface) of the dielectric 20, which is located on an outside in a displacement direction of the electrodes from the position of the front end edge A of the first electrode 11 and closest to the position of the front end edge A of the first electrode 11, in the surface direction of the dielectric 20, $\theta_2$ is an angle (hereinafter referred to as "displacement angle") formed by an imaginary plane N including the front end edge A of the first electrode 11 and the corresponding end edge B of the second electrode 12 with a thickness-wise direction of the dielectric 20, d is a thickness [m] of the dielectric 20, V is the intensity [V] of voltage applied between the first electrode 11 and the second electrode 12, $\theta_1$ is an outgoing angle (see FIG. 3) of an electric field $E_1$ in the plasma forming space 20 at a boundary surface of the dielectric 20, $\in_2$ is a dielectric constant of the dielectric 20, and $E_1$(max) is a maximum value [V/m] of the electric field $E_1$ at the end surface of the electrode.

The displacement angle $\theta_2$ relating to the first electrode 11 and the second electrode 12 is preferably, for example, at least 45°. The displacement quantity L1 between the first electrode 11 and the second electrode 12 and the thickness d of the dielectric 20 A are preferably set in such a manner that a ratio (L1/d) of the displacement quantity L1 to the thickness d of the dielectric 20 is, for example, 1 to 3.

Having such an electrode structure ensures a sufficient electrostatic capacity, so that a required efficiency for forming activated or radical species is surely achieved. In addition, an average value of electronic energy in a discharge field is controlled to a prescribed value or smaller to surely achieve a required efficiency for decomposing ozone. When the displacement angle $\theta_2$ is smaller than 45° on the other hand, the efficiency for forming the activated species is improved, but the electronic energy in the discharge field becomes high, so that decomposition of oxygen and nitrogen in the air is facilitated, and high-concentration ozone and nitrogen oxides are easy to be generated, undesirably.

Equation 3 prescribes a maximum value $E_1$(max) at the end surface of the electrode of an electric field $E_1$ formed by applying voltage V having a prescribed intensity between the first electrode 11 and the second electrode 12 in the electrode structure 10.

Figure 3:
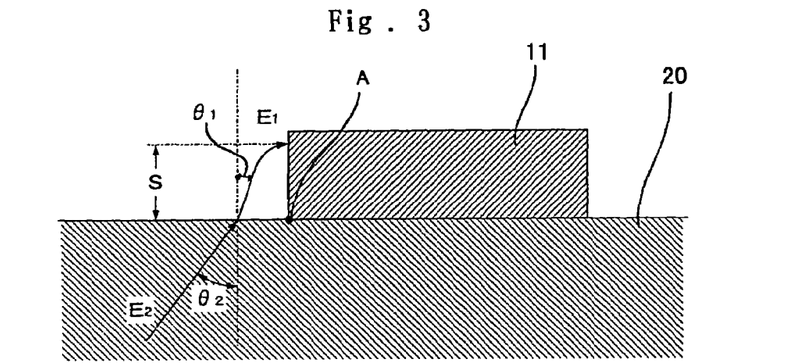
FIG. 3 is a sectional view illustrating, on an enlarged scale, a state of a discharged field at a front end surface of an electrode.

The maximum value $E_1$(max) of the electric field at the end surface of the electrode shown in the right side of Equation 3 is drawn in the following manner. Namely, the electric field $E_2$ in a direction of the displacement angle $\theta_2$ in the dielectric 20 is refracted at the boundary surface between the dielectric 20 (dielectric constant $\in_2$) and the air (dielectric constant $\in_1=1$), which is an atmosphere in the plasma forming space, as illustrated in FIG. 3, and the following relationship is formed between the electric field $E_2$ in the dielectric 20 and an electric field $E_1$ in the air in the vicinity of the first electrode 11. Incidentally, the electric field $E_1$ in the air acts in a direction perpendicular to the front end surface (left end surface in FIG. 2) of the first electrode 11 because the first electrode 11 is conductive.

$$\frac{\tan\theta_1}{\tan\theta_2} = \frac{\varepsilon_1}{\varepsilon_2} \quad \text{(Equation 5)}$$

$$E_1\sin\theta_1 = E_2\sin\theta_2 \quad \text{(Equation 6)}$$

Works of the electric field $E_1$ in the air and the electric field $E_2$ in the dielectric 20 are indicated by potential differences $\Delta V_1$ and $\Delta V_2$, respectively, and the following relationship defined by the following Equation 7 is formed in relation to the voltage V applied between the first electrode 11 and the second electrode 12. In the following Equation 7, S is a height of the end surface where the electric field $E_1$ reaches.

$$V = \Delta V_1 + \Delta V_2 = \frac{S}{\cos\theta_1}E_1 + \frac{d}{\cos\theta_2}E_2 \quad \text{(Equation 7)}$$

The electric field $E_1$ at the end surface of the first electrode 11 is indicated by the following Equation 8 from Equation 6 and Equation 7.

$$E_1 = \frac{\cos\theta_1 \cdot \sin2\theta_2}{S\sin2\theta_2 + d\sin2\theta_1} V \quad \text{(Equation 8)}$$

Accordingly, a position at which the electric field $E_1$ at the front end surface of the first electrode 11 becomes greatest is a position (position of the front end edge A of the electrode) where S is 0, and the maximum value $E_1$(max) of the electric field is indicated by the following Equation 9.

$$E_1(\text{max}) = \frac{\cos\theta_1 \cdot \sin2\theta_2}{d\sin2\theta_1} V \quad \text{(Equation 9)}$$

On the other hand, supposing that a mean free path, which is a distance that an electron can be transferred in the air without colliding with another molecule or atom, is $\lambda$ [μm], energy μ [eV] obtained on the basis of the mean free path of the electron in the air (intensity of the electric field: $E_1$) is drawn by the following equation.

$$\mu = E_1 \lambda [eV] \quad \text{(Equation 10)}$$

In the electrode structure 10 in this embodiment, ceramic or glass is used as the material forming the dielectric 20 as described above. The dielectric constant $\in_2$ thereof may be 8 on the average, and the mean free path $\lambda$ of the electron in the air is about 0.38 μm.

A range of electronic energy easy to cause a collision of an electron with ozone molecule is, for example, 2 to 100 eV in the relationship between the electronic energy μ [eV] in the air and a (dissociation) collision cross section (Masaki Katumoto, Generation and Application of High-Concentration Ozone, Chemical Engineering, The Society of Chemical Engineers, Japan, Dec. 5, 2002, Vol. 66, No. 12, pp. 762–765).

Specifically, when the electronic energy in the discharge field is low, the size of a collision cross section of ozone molecule with the electron is great compared with the collision cross section of, for example, oxygen or nitrogen molecule. As the electronic energy increases, the size of the collision cross section of ozone molecule is liable to become smaller, while the size of the collision cross section of oxygen or nitrogen molecule is liable to become greater. The relationship between the electronic energy and the collision cross section is such that the size of the collision cross section becomes greater as the electronic energy increases, and the electronic energy further increases, the size of the collision cross section becomes small without regard to kind of gases. In other words, the collision cross section has a peak value (maximal value) at electronic energy of a prescribed intensity. With respect to, for example, ozone, the collision cross section shows a peak value (maximal value) when the electronic energy is about 5 eV. When the electronic energy is controlled to, for example, 10 eV or lower, the collision cross section of ozone molecule with electron in the discharge field becomes great, and a collision of an electron with ozone molecule is easy to be caused. As a result, the decomposition of the ozone is facilitated to achieve a high decomposition efficiency.

From such reasons as described above, the maximum value $E_1(max)$ of the electric field at the front end surface of the first electrode 11 may be controlled to at most $26 \times 10^6$ [V/m] from Equation 10 for the purpose of controlling the average value of the electronic energy to, for example, 10 eV or lower.

When the maximum value $E_1(max)$ of the electric field in the air is greater than $26 \times 10^6$ [V/m] on the other hand, a collision of an electron with oxygen or nitrogen molecule rather than ozone molecule is easier to be caused, and the decomposition of oxygen or nitrogen is facilitated. As a result, high-concentration ozone or nitrogen oxides ($NO_x$) are easy to be generated.

In the plasma generator described above, voltage of a prescribed intensity is applied in each pair of electrodes by the voltage applying means, whereby discharge is caused between the first electrode 11 and the second electrode 12 to generate plasma (weak ionization plasma), at a gap between the surface of the dielectric 20 and the first electrode 11 and a gap between the another surface of the dielectric 20 and the second electrode 12 (weak ionization plasma), so that reactions such as excitation, dissociation and ionization take place on atoms or molecules in the air by an inelastic collision of the electron in the plasma, when the air containing harmful substances is introduced into the plasma forming space. As a result, activated or radical species such as, activated oxygen species and the like are formed, and the harmful substances are decomposed by an action of the activated species formed and an action of the plasma itself.

According to the plasma generator described above, since the intensity of electronic energy in the discharge field is controlled to a prescribed value or smaller by employing the electrode arrangement structure satisfying the specific conditions, a collision cross section of ozone molecule becomes great to the electron in the discharge field, so that a collision of the election with the ozone molecule is easy to be caused, with a result that decomposition of ozone is facilitated by the collision of the low-energy electron. As a result, generation of ozone with discharge is surely prevented or controlled to a concentration as extremely low as 0.06 ppm or lower, for example, while the energy of the low-energy electron is increased by increasing the number of times of elastic collisions with gaseous molecules, with a result that such an electron contributes to decomposition of oxygen to surely form activated oxygen species, so that a required essential effect for decomposing or removing harmful substances contained in the air is surely developed by the action of the plasma itself and the action of the activated oxygen species.

In contrast thereto, if a plasma generator is equipped with such an electrode arrangement structure as illustrated in, for example, FIG. 6 or an electrode arrangement structure that for example, the second electrode is in the form of a plane plate that the width dimension thereof is extremely greater than that of each first electrode and functions as a counter electrode common to the respective first electrodes, the maximum value $E_1(max)$ of the electric field at the end surface of the electrode becomes 8 times as much as that having the electrode arrangement structure according to the present invention. As a result, a high electron density may be achieved to be favorable to formation of the activated (oxygen) species and decomposition of organic substances themselves, while the electronic energy in the discharge field becomes great, and a collision cross section of oxygen or nitrogen molecule rather than ozone molecule becomes greater, so that a problem that the a high decomposition efficiency is exhibited to oxygen or nitrogen, and high-concentration ozone or nitrogen oxides are easy to be generated arises. However, such a problem is substantially not caused according to the electrode arrangement structure according to the present invention.

Accordingly, the plasma generator according to the present invention is extremely useful to be applied to, for example, a deodorizing apparatus or air cleaning apparatus from the reasons that an expected decomposing function for organic substances existing in the air is surely achieved with generating less ozone and nitrogen oxides that adversely affect the human body, and minus ions are generated by discharge between the first electrode 11 and the second electrode 12 to achieve a relaxation effect on persons by the minus ions.

In addition, the intensity of electronic energy in the discharge field can be controlled low without greatly lowering an electrostatic capacity by arranging the first electrode 11 and the second electrode 12 in a state displaced from each other, so that an efficiency for forming activated species by an action of plasma is not lowered, as contrasted with that having an electrode arrangement structure as illustrated in, for example, FIG. 6. Accordingly, a desired decomposing effect on harmful substances contained in the air is achieved, and moreover a decomposing effect on ozone is surely developed.

In addition, an effect for controlling or removing ozone generated with the discharge is developed by controlling the electric field at the end surface of the electrode, namely, conducting control of the electronic energy for surely developing the expected ozone-decomposing function, so that there is no need to separately provide a mechanism for treating ozone, and the apparatus itself can be constructed in a small size and advantageously produced.

Although the embodiments of the present invention have been described above, the present invention is not limited to the embodiments, and various modifications may be added thereto.

Figure 4:
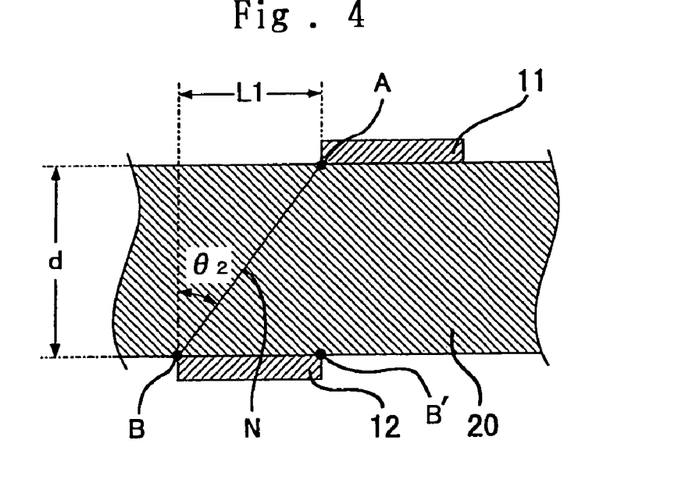
FIG. 4 is a sectional view schematically illustrating the construction of another electrode structure in the plasma generator according to the present invention.

For example, the apparatus may be constructed so as to have an electrode arrangement structure that a position of the rear end edge B' of the second electrode 12 is located on the same line in the thickness-wise direction of the dielectric 20 as a position of the front end edge A of the first electrode 11 as illustrated in FIG. 4. In this embodiment, no problem arises so far as the relationship of Equation 1 to Equation 3 is satisfied. However, the displacement quantity L1 is defined by a separate distance between a position (position of a left end edge of the first electrode 11 in this embodiment) of the front end edge A of the first electrode 11 on the surface of the dielectric 20 and a position (position of a left end edge of the second electrode 12 in this embodiment) of the front end edge B of the second electrode 12 on the another surface of the dielectric 20, which is located on an outside in a displacement direction of the electrodes from the position of the front end edge A of the first electrode 11 and closest to the position of the front end edge A of the first electrode 11, in the surface direction of the dielectric 20.

The same effects as that achieved by the electrode arrangement structure illustrated in FIGS. 1 and 2 can also be achieved in the apparatus having such an electrode arrangement structure.

Figure 5:
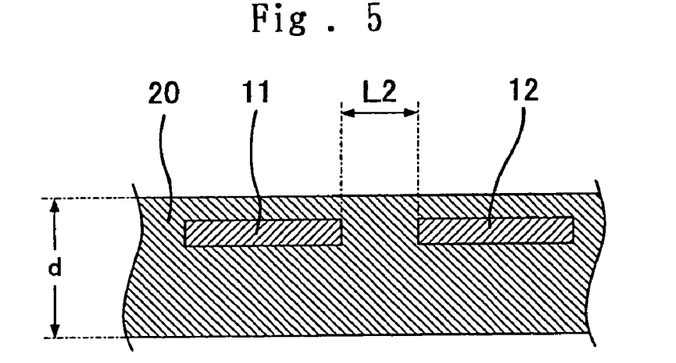
FIG. 5 is a sectional view schematically illustrating the construction of a further electrode structure in the plasma generator according to the present invention.

The apparatus may be constructed so as to have an electrode arrangement structure that the first electrode 11 and the second electrode 12 are embedded in the dielectric 20 in spaced relation from each other so as to be displaced in the same plane in the sectional thickness of the dielectric 20 as illustrated in FIG. 5.

The electrode structure of such a construction is set so as to satisfy the following Equation 4.

$$26 \times 10^6 [V/m] \geq \frac{V}{L2} \quad \text{(Equation 4)}$$

wherein L2 is a separate distance [m] between the first electrode 11 and the second electrode 12, and V is voltage [V] applied between the first electrode 11 and the second electrode 12.

Since an average value of the intensity of electronic energy in a discharge field formed in the vicinity of the surface of the dielectric 20 between the first electrode 11 and the second electrode 12 is controlled to a prescribed value or smaller by having such an electrode arrangement structure, a collision cross section of ozone molecule becomes great to the electron in the discharge field, so that a collision of the election with the ozone is easy to be caused with a result that decomposition of ozone is facilitated by the collision of the low-energy electron. As a result, generation of ozone with discharge is surely prevented or controlled, while the energy of the low-energy electron is increased by increasing the number of times of elastic collisions with gaseous molecules with a result that such an electron contributes to decomposition of oxygen to surely form activated oxygen species, so that a required effect for decomposing or removing harmful substances contained in the air is surely developed by the action of the plasma itself and the action of the activated oxygen species formed.

A sufficient effect is actually achieved even in that having an electrode arrangement structure that both of the first and second electrodes are arranged on the same surface of the dielectric in spaced relation to each other in the surface direction of the dielectric so far as Equation 4 is satisfied. In this embodiment, a whole surface of either one or both of the first and second electrodes is coated with a dielectric film.

In the present invention, the first and second electrodes may have the same width dimensions or dimensions different from each other.

Figure 7:
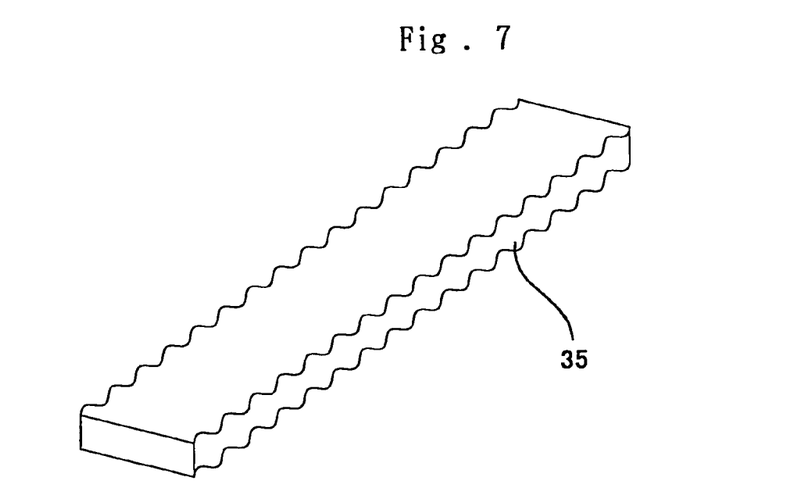
FIG. 7 is a perspective view illustrating the configuration of another exemplary electrode plate or film.

An electrode plate or film 35 for forming the first and second electrodes may be that having a flat form whose side edges are waved as illustrated in FIG. 7. According to the electrode 11 (12) of such a configuration, a more stable discharge field can be formed compared with that (for example, that illustrated in FIGS. 1 to 5) having a flat form whose side edges are in a straight line. In addition, the electrode is prevented from being broken by an action of an excess electric field by being formed into a smooth curve free of pointed portions, so that the expected performance is surely achieved.

Test Examples conducted for confirming the effects of the present invention will hereinafter be described.

TEST EXAMPLE 1

A plasma generator according to the present invention was produced in which an electrode structure having the construction substantially illustrated in FIGS. 1 and 2 was formed. The value of $E_1(max)$ was $24 \times 10^6$ [V/m]. Specific construction conditions are as follows:

(1) First Electrode and Second Electrode:

As first and second electrodes, were used those each having a band plate form having a width of 0.6 mm, a length of 20 mm and a thickness of 0.05 mm and composed of a stainless steel. Two electrodes forming the first electrodes were arranged so as to give a separate distance of 1 mm there between, and the same arrangement of the two electrodes forming the second electrodes was provided.

(2) Dielectric:

As a dielectric, was used a flat plate having a thickness (d) of 0.5 mm, a width of 12 mm and a length of 28 mm and composed of a ceramic, the dielectric constant $\epsilon_2$ of which is 8.

(3) Arrangement Positions of First Electrode and Second Electrode:

A displacement quantity (L1) and a displacement angle ($\theta_2$) between the first electrode and the second electrode were set to 0.5 mm and 45°, respectively.

Voltage of 3 kV was applied between the first and second electrodes to operate the plasma generator, thereby measuring a concentration of ozone by a method described below. As a result, the concentration of ozone was at most 0.06 ppm, so that it was confirmed that a sufficiently high effect for decomposing ozone is achieved.

Air containing acetaldehyde in a proportion of 8 ppm was introduced into the plasma forming space in the plasma generator, and the plasma generator was continuously operated for 30 minutes, thereby confirming that acetaldehyde can be removed in an amount more than natural attenuation by at least 12.5%.

[Measuring Method of Ozone Concentration]

Figure 8:
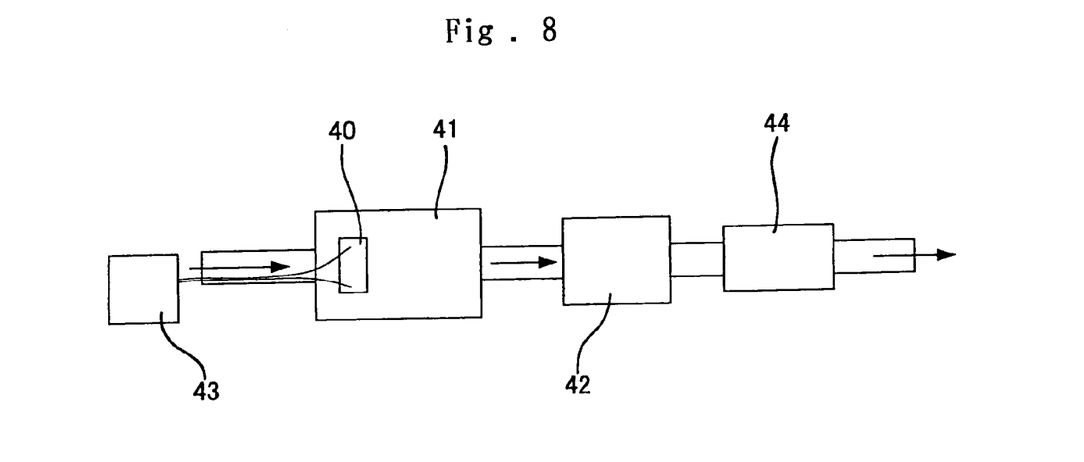
FIG. 8 is a block flow chart illustrating a measuring method of a concentration of ozone in a test example.

The electrode structure (40) produced was arranged in a glass tube (41) having an inner diameter of 50 mm and a length of 250 mm as illustrated in FIG. 8, the air was introduced into the glass tube (41) after at least 5 minutes elapsed from the actuation of the electrode structure (40) to stabilize the operation state of the electrode structure (40), and a concentration of ozone formed in an internal space of the glass tube (41) was measured 10 times by means of an Ozone Monitor (ozone concentration meter) "EG-2001" (EBARA JITSUGYOU) (42) to calculate out an average value thereof. Measuring conditions were such that a flow rate of the air introduced into the glass tube (41) was 1.5 liters/min. In FIG. 8, reference numerals 43 and 44 denote a voltage applying means and an ozone-decomposing device, respectively.

TEST EXAMPLE 2

A plasma generator equipped with an electrode structure of the construction illustrated in FIG. 5 was produced. Specific structures of the first electrode, second electrode and dielectric are the same as those used in Test Example 1. The value of $E_1(max)$ was $20 \times 10^6$ [V/m].

A displacement quantity (L2) between the first electrode (11) and the second electrode (12) was set to 0.15 mm, and both the first electrode and the second electrode were embedded at a position of 0.05 mm from one surface of the dielectric (20).

Voltage of 3 kV was applied between the first and second electrodes to operate the plasma generator, thereby measuring a concentration of ozone. As a result, the concentration of ozone was at most 0.05 ppm, so that it was confirmed that a sufficiently high effect for decomposing ozone is achieved.

Air containing ammonia in a proportion of 20 ppm was introduced into the plasma forming space in the plasma generator, and the plasma generator was continuously operated for 30 minutes, thereby confirming that ammonia can be removed in an amount more than natural attenuation by at least 10%.

COMPARATIVE TEST EXAMPLE 1:

A comparative plasma generator equipped with an electrode structure (that of the construction illustrated in FIG. 6) of the same construction as in Test Example 1 except that the first electrode and the second electrode were arranged in a state that central positions in arrangement of these electrodes were aligned with each other.

Voltage of 3 kV was applied between the first and second electrodes to operate the plasma generator, thereby measuring concentrations of ozone and nitrogen oxides. As a result, the concentration of ozone was 0.2 ppm, so that it was confirmed that generation of ozone with the discharge could not be prevented. The reason for it is considered to be attributable to the fact that the energy state of the electron in the discharge field becomes a state that a higher decomposing effect is exhibited on oxygen rather than ozone because the maximum value of the intensity of the electric field becomes excess, so that decomposition of oxygen in the air is facilitated.

What is claimed is:

1. A plasma generator, comprising:
a plasma forming space into which air is introduced;
a dielectric provided in the plasma forming space; and
band plate-like first and second electrodes arranged in opposed relation to each other on respective surfaces of the dielectric in the plasma forming space,
wherein plasma is generated by discharge caused by applying voltage between the first and second electrodes, and the first and second electrodes are provided on the respective surfaces of the dielectric so as to be relatively displaced in a surface direction of the dielectric so as to satisfy equation 1, equation 2 and equation 3:

$$\tan\theta_2 = \frac{L1}{d} \quad \text{(Equation 1)}$$

$$\tan\theta_1 = \frac{1}{\varepsilon_2}\tan\theta_2 \quad \text{(Equation 2)}$$

$$26 \times 10^6 [\text{V/m}] \geq \frac{\cos\theta_1 \cdot \sin 2\theta_2}{d\sin 2\theta_1} V = E_1(\max) \quad \text{(Equation 3)}$$

where:
L1 is a separation distance in the surface direction of the dielectric between a front end edge of the first electrode and a corresponding end edge of the second electrode, which is located on an outside in a displacement direction of the electrodes from the front end edge position of the first electrode and which is closest to the front end edge position of the first electrode,
$\theta_2$ is an angle formed by an imaginary plane including the front end edge of the first electrode and the end edge of the second electrode across a thickness of the dielectric,
d is a thickness [m] of the dielectric,
V is an intensity [V] of the voltage applied between the first and second electrodes,
$\theta_1$ is an outgoing angle of an electric field in the plasma forming space at a boundary surface of the dielectric,
$\varepsilon_2$ is a dielectric constant of the dielectric, and
$E_1(\max)$ is a maximum value [V/m] of the electric field at the end surface of the electrode.

2. The plasma generator according to claim 1, wherein the corresponding end edge of the second electrode is a rear end edge of the second electrode.

3. The plasma generator according to claim 1, wherein the corresponding end edge of the second electrode is a front end edge of the second electrode.

4. The plasma generator according to claim 1, wherein the angle $\theta_2$ is at least 45°.

5. The plasma generator according to claim 1, wherein a ratio (L1/d) of the separation distance L1 to the thickness d of the dielectric is 1 to 3.

6. The plasma generator according to claim 4, wherein a ratio (L1/d) of the separation distance L1 to the thickness d of the dielectric is 1 to 3.

7. The plasma generator according to claim 1, wherein the voltage applied between the first and second electrodes is 2.5 to 3.5 kV.

8. The plasma generator according to claim 4, wherein the voltage applied between the first and second electrodes is 2.5 to 3.5 kV.

9. The plasma generator according to claim 5, wherein the voltage applied between the first and second electrodes is 2.5 to 3.5 kV.

10. The plasma generator according to claim 6, wherein the voltage applied between the first and second electrodes is 2.5 to 3.5 kV.

11. The plasma generator according to claim 3, wherein a ratio (L1/d) of the separation distance L1 to the thickness d of the dielectric is 1 to 3.

12. The plasma generator according to claim 2, wherein the voltage applied between the first and second electrodes is 2.5 to 3.5 kV.

13. The plasma generator according to claim 3, wherein the voltage applied between the first and second electrodes is 2.5 to 3.5 kV.

14. The plasma generator according to claim 2, wherein the angle $\theta_2$ is at least 45°.

15. The plasma generator according to claim 3, wherein the $\theta_2$ is at least 45°.

16. The plasma generator according to claim 2, wherein a ratio (L1/d) of the separation distance L1 to the thickness d of the dielectric is 1 to 3.

* * * * *